US006851426B1

(12) United States Patent
Strömberg

(10) Patent No.: US 6,851,426 B1
(45) Date of Patent: Feb. 8, 2005

(54) ARRANGEMENT IN VENTILATORY TREATMENT OF THE LUNGS

(75) Inventor: Stefan Strömberg, Sigtuna (SE)

(73) Assignee: ANEO AB (SE)

( * ) Notice: Subject to any disclaimer, the term of this patent is extended or adjusted under 35 U.S.C. 154(b) by 0 days.

(21) Appl. No.: 09/979,987

(22) PCT Filed: May 25, 2000

(86) PCT No.: PCT/SE00/01067
§ 371 (c)(1),
(2), (4) Date: Mar. 25, 2002

(87) PCT Pub. No.: WO00/74757
PCT Pub. Date: Dec. 14, 2000

(30) Foreign Application Priority Data

Jun. 3, 1999 (SE) .............................................. 9902051

(51) Int. Cl.[7] .............................................. F16K 31/02
(52) U.S. Cl. .......................... 128/204.21; 128/205.24; 128/205.25; 128/207.14; 128/207.18
(58) Field of Search ........................ 128/204.18, 204.21, 128/205.24, 205.25, 207.14–207.18, 200.14, 200.24, 203.12, 204.22, 204.23, 204.26, 205.23; 600/529, 531–543

(56) References Cited

U.S. PATENT DOCUMENTS

| 3,844,280 A | | 10/1974 | Smythe | |
|---|---|---|---|---|
| 3,961,627 A | | 6/1976 | Ernst et al. | |
| 5,564,416 A | * | 10/1996 | Jones | 128/204.21 |
| 6,000,397 A | * | 12/1999 | Skog | 128/204.22 |
| 6,076,523 A | * | 6/2000 | Jones et al. | 128/205.11 |

* cited by examiner

*Primary Examiner*—Glenn K. Dawson
(74) *Attorney, Agent, or Firm*—Banner & Witcoff, Ltd.

(57) ABSTRACT

The invention relates to an arrangement in ventilatory treatment of the lungs of a living creature (2) under anaesthesia, comprising valve equipment (4) devised for carrying an insufflation gas and/or an insufflation gas mixture from a unit for pulmonary ventilation (3) into the lungs and airways (2a) of the living creature and permitting expiration of gas and/or gas mixture held in the airways and gas measurement equipment (6) in the sensor unit (61, 62, 63). The said valve equipment (4) and a combination of the said sensor units (61, 62, 63) are arrayed close together. They are connected to an end section of a bundle of hoses (30) from the unit for pulmonary ventilation, and the said sensor units are located closer to the living creature (2) than the said valve equipment (4).

14 Claims, 1 Drawing Sheet

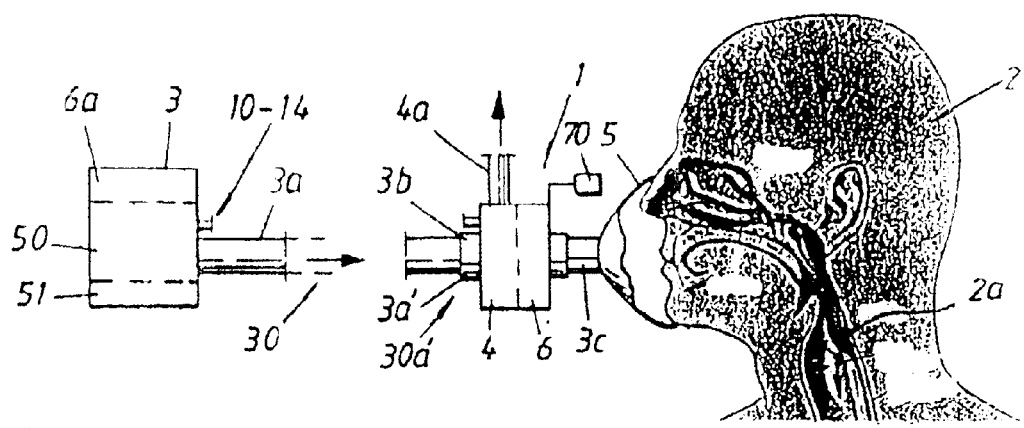
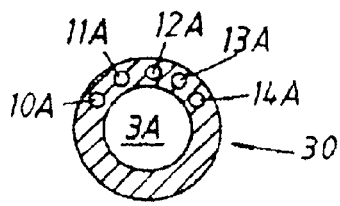
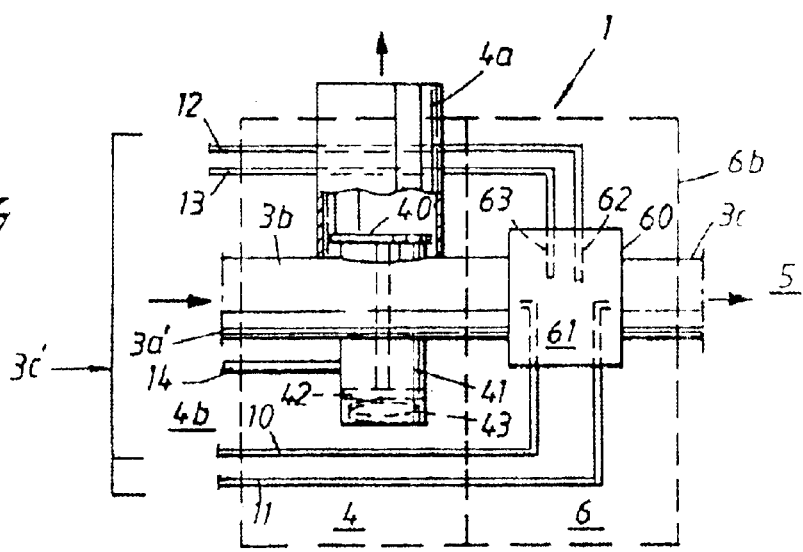
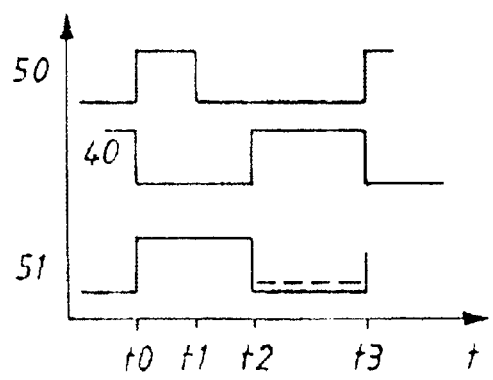

ARRANGEMENT IN VENTILATORY TREATMENT OF THE LUNGS

This is a U.S. National Phase Application Under 35 USC 371 and applicant herewith claims the benefit of priority of PCT/SE00/01067 filed May 25, 2000, which was published Under PCT Article 21(2) in English and Application No. 9902051-3 filed in Sweden on Jun. 3, 1999.

FIELD OF THE INVENTION

The present invention relates to an arrangement in ventilatory treatment of the lungs of a living creature and was primarily developed for use during anaesthesia induced by intravenous infusion of a liquid anaesthetic agent.

The arrangement according to the present invention comprises valve equipment devised to carry an insufflation gas, and/or an insulation gas mixture, from a unit for pulmonary ventilation into the lungs and airways of the living creature and permit controlled expiration of gas, and/or gas mixture, held in the airways.

The arrangement can additionally comprise one or a plurality of sensor units in gas-measuring equipment. One of these can be devised to sense a gas velocity-related pressure gradient in measurement of the velocity and duration of the insufflation gas.

Another sensor unit, or the same one cited above, can be devised to sense a gas velocity-related pressure gradient in measurement of the velocity of expired gas and the duration of the expiratory phase.

An additional sensor can be devised to measure the insufflation gas's and/or expiration gas's pressure and/or pressure variation over time.

An additional sensor can be devised to divert part of the gas mixture for analysis in measurement of the presence of and/or percentage of one or a plurality of gas components in the gas mixture.

PRIOR ART

Arrangements of this kind are previously known from a number of different embodiments and are normally connected to a lung ventilator and/or a unit for ventilating the lungs.

A previously known lung ventilator, used for ventilating the lungs of a patient under anaesthesia, has a first hose, devised for insufflating a patient with gas or a gas mixture, between the lung ventilator and the patient, and the hose has a ventilator insufflation valve connected to it.

Lung ventilators of this kind and for the cited use also have a second hose, with the same cross-section as the first hose, between the lung ventilator and the patient to carry expired gas or a gas mixture to the lung ventilator and an expiratory valve connected to the ventilator.

The end of the hoses away from the ventilator are bundled and coupled to a patient connection part to form a sealed, controlled path of flow for insufflation gas and for expired gas.

Connection parts of this kind are available in different versions, such as a tracheal tube and laryngeal mask.

During an initial part of insufflation with lung ventilators of this kind and for the cited use, the insufflation valve opens while an expiratory valve remains closed throughout the entire insufflation phase. The expiratory valve is open throughout the entire expiratory phase, and the insufflation valve is shut. An inspiratory pause, during which both the insufflation valve and the expiratory valve are closed, may also occur.

The valves, which are made to control the insufflation phase and the expiratory phase in this way, are both built into the lung ventilator's basic unit, so two different hoses for insufflation gas and expired gas extend from the lung ventilator's basic unit.

As regards the significant properties of the present invention, it can be noted that utilisation of one or as plurality of gas measuring devices and one or a plurality of sensor units attached to same is previously known.

Examples of such sensor units were cited above under the heading "Field of the invention".

As regards the measures involved in the present invention, it can be noted that in the field for utilisation, of units for pulmonary ventilation of non-anaesthetised living creatures, the introduction of a control valve and a measuring device with a requisite flow sensor, in the form of a device for measuring gas flow and gas pressure in the ventilator gas's direction of flow near the creature or patient, is previously known from the patent publication U.S. Pat. No. 3,961,627.

Here, the mechanism for driving the valve consists e.g. of a servo-motor receiving signals from a valve control unit.

DESCRIPTION OF THE PRESENT INVENTION

Technical Problems

As regards the circumstance that the technical considerations someone well-versed in this art has hitherto been forced to make in order to offer a solution to one or more technical problems arising, insight into the measures, and/or sequence of measures to be adopted, is initially necessary, and a choice of the required means is necessary. With a view thereto, the following technical problems should be relevant in achieving the present invention.

With a view to the prior art, as described above, the ability to set forth an arrangement, consisting of controllable valve equipment combined with a plurality of sensor units, all capable of being located very close to the creature, should be viewed as a technical problem in the ventilatory treatment of a living creature under anaesthesia induced by the intravenous infusion of an anaesthetic agent in liquid form.

The ability to create conditions in which the arrangement offers less dead space than known equipment for this application is also a technical problem.

Realisation of the importance of and advantages associated with being able to offer utilisation of only one hose, devised with a cross-section for carrying an insufflation gas or a gas mixture from the lung ventilator to a patient in a state of deep anaesthesia induced by the infusion of a liquid drug, and additionally a number of hoses, with a considerably smaller cross-section, for determining different parameters for the gas or gas mixture, and for controlling valve equipment from the lung ventilator via a valve in the lung ventilator, is also a technical problem.

A technical problem is also involved in creating such conditions with an arrangement of this kind that valve equipment devised for the purpose and an array of combined sensor units devised for the purpose for evaluating a plurality of gas-or gas mixture-related parameters can be installed close together and placed near the living creature requiring ventilatory treatment of the lungs during anaesthesia and close to a connection part used by the creature or patient.

A technical problem is also involved in being able to realise the importance of coupling the valve equipment and the combined sensor unit array in series and connecting them to the end section of a bundle of hoses, or a plurality of hoses with differing cross-sections, from the lung ventilator unit.

A technical problem is also involved in being able to realise the importance of positioning the said combined sensor unit array closer to the said living creature than the said valve equipment.

A technical problem is also involved in being able to realise the importance of and advantages associated with integrating the said valve equipment and the said combined sensor unit array into a single unit.

Moreover, a technical problem should be involved in being able to realise the importance of and advantages associated with devising the sensor unit array or a sensor unit part of the unit for fixed but easily detachable connection to a patient connection part.

In addition, a technical problem is involved in being able to create conditions, using simple means, facilitating the cleaning of used valve equipment and a combined sensor unit array and having them designed in such a way that they cannot be turned the wrong way or mounted incorrectly.

A technical problem is also involved in being able to realise the importance of and advantages associated with having the said valve equipment, or a valve equipment part of the unit, devised for connection to the outer end section of an insufflation hose, to a number of sensor unit hoses and to a hose for controlling the valve equipment.

A technical problem is also involved in being able to realise the importance of giving the said end section the shape of a first hose, with a cross-section devised for insufflation gas, a number of other hoses, with cross-sections suitable for gas measurement (comprising measurement of both pressure and flow) and a hose for controlling the valve equipment, the second number of hoses and the valve equipment hose being peripheral to the first hose in forming a bundle of hoses.

A technical problem is also involved in being able to realise the importance of having the said end section consist of a first hose, with a large cross-section devised for insufflation gas, connected to a lung ventilator unit and integrating the other hoses, with smaller cross-sections, two or three of these other hoses being, devised to be able, by means of pressurisation by the combined sensor unit array, to offer measurement of a gas velocity-related pressure gradient and measurement of pressure, one hose is devised for diverting part of the gas or gas mixture to measurement equipment for gas analysis by means of gas sampling and one hose is connected to the valve equipment for creating, by means of pressurisation by the valve arrangement, an insulation phase, an expiratory phase, pressure relief and, if needed, suitable counter-pressure throughout the entire expiratory phase.

A technical problem is also involved in realising the advantages associated with the presence of and position of an underpressure valve which, at a selected underpressure in the insufflation hose, opens a valve to room air for an inhalation by the living creature or patient.

The Solution

In order to solve one or more of the aforesaid technical problems, the present invention is based on an arrangement in the ventilatory treatment of the lungs of a living creature under anaesthesia comprising valve equipment devised for carrying an insufflation gas, and/or a mixture of insufflation gas, from a lung ventilator unit into the lungs and airways of the living creature and allowing expiration of a gas and or gas mixture held in the airways and one or more sensor units in the gas measurement equipment, one sensor unit being devised to sense the gas velocity-related pressure gradient in measurement of the velocity of the insufflation gas and duration of the insufflation phase.

One and the same sensor unit can be devised for sensing the gas velocity-related pressure gradient in measurement of the velocity of expired gas and the duration of the expiratory phase.

A second sensor is devised for measuring pressures and/or pressure variations over time.

A sensor unit can be devised to divert part of the gas mixture for gas analysis for measuring the presence of and/or percentage of one or more gas components in the gas mixture.

In order to solve one or more of the aforesaid technical problems, the present invention particularly cites that the said valve equipment and a combination of sensor unit arrays shall be located close together, that they be connected to the end section of a bundle of hoses from a unit for pulmonary ventilation and that the said sensor units be located closer to the said living creature than the said valve equipment.

As preferred embodiments within the scope of the invention concept, we cite that the said valve equipment and the said sensor unit array shall be integrated into a single unit.

We further cite that sensor units, or a sensor unit part of the unit, shall be devised for connection to a creature connection part.

We further cite that valve equipment, or a valve equipment part of the unit, shall be devised for connection to the outer free end section of a bundle of hoses.

We further cite that the said end section shall have the shape of a first hose, with a cross-section suitable for insufflation gas, and a number of internal lumens, with cross-sections suitable for gas measurement and valve control.

The end section is formed from a first hose, connected to a unit for pulmonary ventilation, and integrated with internally extending lumens with smaller cross-sections, two of the lumens are devised for measuring pressure gradient, possibly one of the lumens is for measuring pressure, one of the lumens is for gas sampling and one of the lumens, for pressurising the valve equipment, is also able to serve as a pressure relief or act on minor counterpressure during expiration.

We further cite that the valve equipment and the said sensor unit array are mutually devised so they can only interconnect in one way and one way only.

The valve equipment shall have means for coupling to the hose with multiple internal lumens, and the combination of sensor unit array shall have means for connection to the connection part for the living creature.

We particularly propose that the said coupling means be distinctively shaped so they cannot be confused with each other.

The said valve equipment can be controlled from the lung ventilator by a lung ventilator valve capable of pressuring the hose so valve equipment, during a first pressurisation in the insufflation phase, forces insufflation gas down into the airways and serves as a pressure relief, and the valve equipment, during a second lesser pressurisation in the expiratory phase, supplies a counter pressure, i.e. a PEEP pressure, or, no pressurisation occurs in the expiratory phase.

Advantages

The main advantages which can be regarded as characteristic of an arrangement used in ventilatory treatment of the lungs according to the present invention are that conditions are accordingly created for efficient co-ordination of valve equipment and an array of sensor units, enabling both to be placed close to a living creature, possibly with the aid of a connection part, and conditions are created for the use of only one hose, between a unit for pulmonary ventilation and the living creature or patient being treated by intravenous infusion of a liquid anaesthetic agent, for the ventilatory gas, for the ventilatory gas, thereby providing an opportunity for gas expired by the creature to pass from the valve equipment out into room air in the immediate vicinity of the patient without any expired gas contaminating the lung ventilator.

Specially devised connectors eliminating the risk of erroneous coupling are also proposed.

The features deemed to be the main characteristics of an arrangement according to the present invention are evident from the characterising part of claim 1.

BRIEF DESCRIPTION

One currently proposed embodiment of an arrangement, devised for use in the ventilatory treatment of the lungs of a living creature, will now be described in greater detail, referring to the enclosed drawing in which FIG. 1 shows a lateral view of a living creature to whose mouth and nose area a connection part, in the form of a face mask with mounted valve equipment and a combination of sensor unit arrays according to the present invention, has been applied, FIG. 2 shows a proposed cross-section for a hose with internal lumens between the arrangement and a unit for pulmonary ventilation, FIG. 3 is a schematic cross-section of valve equipment and a number of sensor unit arrays, according to FIG. 1, integrated into a single unit, and FIG. 4 shows the chronological activation of the insufflation phase and the expiratory phase and the action of the valve equipment.

DESCRIPTION OF THE PREFERRED EMBODIMENT

FIG. 1 shows the principles for use of an arrangement 1 devised according to present invention.

The arrangement 1 is devised for use in the ventilatory treatment of the lungs of a living creature 2.

The ventilatory treatment of the lungs is to be provided during anaesthesia induced by the intravenous infusion of a liquid anaesthetic agent into the bloodstream of the patient 2.

In these circumstances, utilisation of a unit for pulmonary ventilation 3 is required as well as checks on various therapeutic and diagnostic parameters.

The unit for pulmonary ventilation 3 according to the present invention has been supplemented so there is only one hose with a large cross-section, an insufflation hose 3a, between the unit 3 and the arrangement 1.

The unit 3 with requisite means for evaluating therapeutic and/or diagnostic parameters, would have the features shown and described in Swedish patent application 9901688-3.

The contents of the said patent application shall therefore be regarded as part of the contents of the present application.

The arrangement 1, according to the present invention, contains the valve equipment 4. It is devised to carry an insufflation gas, and/or an insufflation gas mixture, from a unit for pulmonary ventilation 3, into the lungs and airways 2a of the living creature and allow expiration of gas and/or gas mixture, under positive pressure, held in the airways.

The insufflation gas can consist of pure air, air mixed with oxygen or oxygen alone.

This insufflation gas passes a short hose section 3b, in addition to the hose 3a, through the arrangement 1a and a short hose section 3c in order to pass, via a connection part 5, through the airways 2a down into the lung area. The valve 40 is closed by pressurisation from a hose 14.

When insufflation gas held in the airways is expired, expired gas is allowed to pass the said connection part 5, the hose section 3c and, with the aid of a valve 40 in the valve equipment 4, exit through an outlet with a hose section 4a into room air.

Expired gas will pass this way, as an insulation valve 50 in the unit for pulmonary ventilation 3 assumes a closed position, thereby preventing expired gas from passing through hose section 3b and the hose 3a into unit 3. The valve 40 is now relieved from pressure.

The valve equipment 4 is also controllable in such a way that the valve equipment serves as pressure relief during the insufflation phase by allowing the unit 3, via a valve 51, to pressurise a hose 14 with a preset maximum pressure. In this way, pressure relief is activated when pressure exceeds e.g. 60–100 cm $H_2O$.

The valve equipment 4 is also devised to create a lower positive pressure, i.e. a PEEP pressure of e.g. 0–20 cm $H_2O$, by means of lower pressure on the hose 14 during the expiratory phase.

This will be described in greater detail in conjunction with FIG. 4.

The arrangement 1 also has gas-measuring equipment in the sensor unit or a sensor unit array of a plurality of sensor units 6 in which one or more gas-measuring units can advantageously be built into the unit for pulmonary ventilation 3 as in block 6a.

The sensor unit 6, with associated gas-measuring equipment 6a, consists here of a number of known, coordinated and integrated sensor units.

The embodiment according to FIG. 3 shows one way to devise a measurement chamber 60 in which a number of sensor units are combined in a sensor unit array.

The sensor unit array or measurement chamber 60 shall, thus, incorporate a plurality of intercombined sensor units. The following describes an example of one such combination.

A sensor unit 61 can be devised for sensing a gas velocity-related pressure gradient in measurement of the velocity of the insufflation gas and the duration of the insufflation phase.

This is illustrated by two orifices facing away from each other for two or more hoses 10, 11.

It is assumed here that the flow of gas in one direction (3b–3c) causes an increase in pressure in the hose 10 and a drop in pressure in the hose 11 and that the pressure gradient provides a measure of gas velocity.

Another sensor unit, or the sensor unit 61 above, can be devised for sensing the gas velocity-related pressure gradient in measurement of the velocity of expired gas and the duration of the expiratory phase.

An additional sensor unit 62 can be devised for measuring, via a hose 12, the pressure of the gas and/or chronological variations in pressure.

A sensor unit 63 can be devised to divert part of the gas mixture for measuring the presence of and/or percentage of one or more gas components in the gas mixture.

Measurement values received in the form of pressurisation via the hoses 10, 11 and 12 and a percentage of the gas mixture via the hose 13 are sent to the unit 3 which contains requisite means and equipment for evaluating therapeutic and/or diagnostic parameters.

The invention is based on the circumstance that the said valve equipment 4 and selected combination of sensor unit arrays in the said sensor unit 6 or measurement chamber 60 are tightly spaced.

They are connected to an end section 3a' for an insufflation gas hose 3a from a unit for pulmonary ventilation 3, and the said sensor unit 6 is located closer to the living creature 2 than the said valve equipment 4.

FIG. 3 shows that the said valve equipment 4 and the said sensor unit 6 are integrated into a single unit 1.

The sensor unit 6, or a sensor unit part of the unit or the arrangement 1, is devised for co-operation with said connection part 5.

The valve equipment 4, or a valve equipment part of the unit 4b, is primarily devised for co-operation with the end section 3a' of a hose 3a.

FIG. 1 shows that a bundle of hoses 30 arranged between the arrangement 1 and the unit 3.

This bundle of hoses 30 can consist of a number of individual coordinated or uncoordinated hoses and is dominated by the insufflation hose 3a with a large cross-section.

We propose that all hoses preferably be integrated with one another (or bound together).

FIG. 2 shows a proposed cross-section of a hose having a wall containing multiple internal lumens 30, connecting the unit for pulmonary ventilation 3 to the arrangement 1, especially part 4b in unit 4. Here, the said end section 30a' has the shape of a first lumen 3a, devised for insufflation gas, whose cross-section has been designated 3A.

There are a number of additional internal lumens with a smaller cross-section 10A, 11A, 12A, 13A, 14A, devised for gas measurement and valve control, and they can be oriented e.g. as shown in FIG. 2.

Thus, five lumen cross-sections designated 10A, 11A, 12A, 13A, 14A are used for the proposed purpose and combined in the measurement chamber with the sensor units 61, 62 and 63, and they are devised for interaction with the hoses 10–14 in the arrangement 1.

The hoses 10 and 11 are connected to the measurement chamber 60 and the sensor unit 6 in measurement of the velocity of insufflation gas and the duration of the insufflation phase and of the velocity of expired gas and the duration of the expiratory phase, both hoses being devised for opposite directions of flow.

The hose 14 is devised for generating a positive pressure, variable between two or three positions, from the unit for pulmonary ventilation 3.

FIG. 4 shows the chronological course of events for activation and deactivation of two unit valves 50, 51 and the valve equipment valve 40.

An insufflation valve 50 in the unit 3 is activated at time t0, causing insufflation gas to flow through the hose 3a.

At the same time, a control valve 51 is activated, causing pressure in the hose 14 to rise to a first pre-set value.

This pressure acts on the valve equipment 4, causing the valve 40 to serve as a pressure relief valve and permitting insufflation gas to exit at a positive pressure exceeding 60–100 cm $H_2O$ through an outlet 4a.

The insufflation valve 50 closes at time t1, and insufflated gas is able to circulate in the airways 2a until time t2.

The insufflation phase concludes at time t2, when the control valve 51 causes pressure in the hose 14 to terminate, and an expiratory phase begins.

The expiratory phase concludes at time t3 when the control valve 51 again increases pressure in the hose 14, and the valve 50 is activated.

During the expiratory phase t2 to t3, the valve equipment 4 can, via the line 14 be acted, on by a lower pressure in order to create an expiratory phase against a selected counter-pressure, i.e. a PEEP pressure, designated by the dashed line.

The PEEP pressure will accordingly be the lowest pressure in the airways 2a at the end of the expiratory phase.

Thus, the insufflation phase and, when necessary, the expiratory phase, work under excess pressure monitoring or alternately against a counter-pressure via the valve 40 which is kept closed by appropriate pressure through appropriate positive pressure in a chamber 41 and a piston 42.

The times t1, t2, t3 and t4 can obviously vary somewhat along the time axis.

The end section 30a' is formed by first internal lumen 3a, with a large cross-section connected to a unit for pulmonary ventilation 3 plus other, integrated internal lumens with much smaller cross-sections 10A, 11A, 12A, 13A, 14A.

The invention is also based on the interaction between a hose section 30a' and a first coupling part in a two-part connector in which the second part is attached to side 4b of the unit 4.

In a similar fashion, the connection part 5 interacts with a first coupling part in a two-piece connector in which the second part is attached to side 6b of the sensor unit 6.

The coupling parts shown here can be simple connectors formed by threading/inserting a section of hose over or inside a section of hose.

The valve equipment 4 and the said combination of sensor units 6 are distinctively shaped (FIG. 1) so they can only interconnect in and one way only.

The valve equipment 4 has connectable connector means for connection to the hose 30 with multiple internal lumens.

The combination of sensor units 6 has connector means for connection to the connection part 5.

It is important for the said connector means to be distinctively shaped so they cannot be erroneously interconnected.

When the living creature or the patient phase begins spontaneous breathing during the recovery phase, an under-pressure valve 70 offers unimpeded breathing. This under-pressure valve can be attached to the arrangement 1 and offer free inhalation of ambient air.

In an alternative embodiment, PEEP pressure could instead be regulated and kept constant, instead of being a reduced pressure in the hose 14, by utilisation of a torsion spring 43 shown in FIG. 3 under the valve plate or piston 42. The torsion spring's spring force can be adjusted with means, not shown in the Fig., thereby permitting regulation of the PEEP pressure.

The invention is obviously not limited to the exemplifying embodiment above but can be modified within the scope of the invention concept as illustrated in the following claims.

What is claimed is:

1. An arrangement in ventilatory treatment of the lungs of a living creature under anaesthesia, comprising valve equipment devised for carrying an insufflation gas from a unit for pulmonary ventilation into the lungs and airways of the living creature and permitting expiration of the gas held in the airways, a connection part adapted to contact the living creature to direct the insufflation gas into the lungs and airways of the living creature, gas measurement equipment adherent to a sensor unit for sensing a gas velocity-related pressure gradient in measurement of the velocity of the insufflation gas and the duration of the insufflation phase, a sensor unit for sensing the gas velocity-related pressure gradient in measurement of the velocity of expired gas and the duration of the expiratory phase, a sensor unit devised for measuring the pressure of the gas and/or variations in pressure over time and a sensor unit devised to divert a part of the gas for measurement of the presence of and/or percentage of one or more gas components in the gas, wherein said valve equipment and a combination of said sensor units are arrayed closely together and integrated into a single unit connected to an end section of a hose including a wall and a plurality of internally extending lumens, said sensor units are located closer to the connection part than said valve equipment, said end section of said hose is spaced from the unit for pulmonary ventilation, has a hose-like shape and includes openings for the plurality of lumens that comprise a first lumen opening having a first cross-section and being connected to the unit for receiving the insufflation gas and pulmonary ventilation, and additional lumen openings having cross-sections that are smaller than said first cross-section, said additional lumen openings each being integrated with said first lumen opening in said end section for gas measurement and valve control, said additional lumens include lumens devised for measuring pressure gradient, a lumen for measuring pressure, a lumen for gas sampling and a lumen for counter-pressure acting on the valve equipment.

2. The arrangement according to claim 1 wherein at least a portion of one of said sensor units is devised for connection to the connection part for the living creature.

3. The arrangement according to claim 2, wherein the connection part is adapted to be placed outside the creature and attachable to the one of said sensor unit.

4. The arrangement according to claim 1, wherein the valve equipment and said sensor units are distinctively shaped so they can only interconnect in one way.

5. The arrangement according to claim 1, wherein the valve equipment has a connector means for the hose including said internal lumens.

6. The arrangement according to claim 1, wherein the combination of sensor units has a connector means for connection to the connection part for the living creature.

7. The arrangement according to claim 5 or 6, wherein said connector means are distinctively shaped so they cannot be confused with each other.

8. The arrangement according to claim 7, wherein the valve equipment provides pressure relief when pressurisation occurs during the insufflation phase.

9. The arrangement according to claim 7, wherein the valve equipment serves as counter-pressure when pressurisation occurs during the expiratory phase.

10. The arrangement according to claim 1, wherein the said valve equipment is controllable by pressurisation of a control hose.

11. The arrangement according to claim 1, wherein an underpressure valve is connected to the arrangement.

12. The arrangement according to claim 1, wherein said valve equipment comprises a PEEP valve.

13. The arrangement according to claim 1, wherein said insufflation gas includes an insufflation gas mixture.

14. The arrangement according to claim 1, wherein said expired gas includes an expired gas mixture.

* * * * *